(12) United States Patent
Wassenaar et al.

(10) Patent No.: US 11,191,701 B2
(45) Date of Patent: Dec. 7, 2021

(54) EXCIPIENT FREE N-ACETYL GLUCOSAMINE TABLETS AND METHOD OF MAKING

(71) Applicant: Purepharm Inc., Toronto (CA)

(72) Inventors: Willem Wassenaar, Toronto (CA); Brandon Wren, Scarborough (CA)

(73) Assignee: PurePharm, Inc., Toronto (CA)

( * ) Notice: Subject to any disclaimer, the term of this patent is extended or adjusted under 35 U.S.C. 154(b) by 59 days.

(21) Appl. No.: 16/444,800

(22) Filed: Jun. 18, 2019

(65) Prior Publication Data
US 2019/0380912 A1    Dec. 19, 2019

(30) Foreign Application Priority Data
Jun. 19, 2018 (CA) ................................. CA 3008722

(51) Int. Cl.
| | |
|---|---|
| A61J 3/10 | (2006.01) |
| A61K 9/20 | (2006.01) |
| A61K 31/7008 | (2006.01) |
| B29C 43/00 | (2006.01) |
| B29C 43/02 | (2006.01) |

(52) U.S. Cl.
CPC ............... *A61J 3/10* (2013.01); *A61K 9/2095* (2013.01); *A61K 31/7008* (2013.01); *B29C 43/003* (2013.01); *B29C 43/02* (2013.01)

(58) Field of Classification Search
CPC ...... A61J 3/10; A61K 31/7008; A61K 9/2095
See application file for complete search history.

(56) References Cited

U.S. PATENT DOCUMENTS

| | | | | |
|---|---|---|---|---|
| 3,697,652 A | * | 10/1972 | Rovati | ................... C07H 13/04 |
| | | | | 514/62 |
| 5,843,919 A | | 12/1998 | Burger | |
| 2007/0259094 A1 | * | 11/2007 | Wassenaar | ................ A23F 5/14 |
| | | | | 426/590 |

(Continued)

FOREIGN PATENT DOCUMENTS

| | | | | |
|---|---|---|---|---|
| EP | 1075836 A2 | * | 2/2001 | ............. A61K 8/735 |
| JP | 06218028 A | * | 8/1994 | ........... A61K 9/2095 |

(Continued)

OTHER PUBLICATIONS

Waterman et al. (Impurities in Drug Products Chapter 4 in: Handbook of Isolation and Characterization of Impurities in Pharmaceuticals 2003 pages; 3 pages) (Year: 2003).*

(Continued)

*Primary Examiner* — Ernst V Arnold
(74) *Attorney, Agent, or Firm* — Colleen M. Schaller; Howson & Howson LLP

(57) ABSTRACT

The present invention is a method of making excipient free N-Acetylglucosamine tablets and also the excipient free N-Acetylglucosamine tablets in a variety of sizes, in particular 10 gram tablets. These excipient free tablets are palatable and suitable for consumption by horses, smaller animals and humans. In the method of making these tablets, of N-Acetylglucosamine powder is mixed with a specific amount of water, to bring about a moldable mass which is formed into suitably sized tablets through compression in a tablet mold. The solvent water is then allowed to evaporate leaving behind an excipient free N-Acetylglucosamine tablet.

4 Claims, 1 Drawing Sheet

(56) References Cited

U.S. PATENT DOCUMENTS

2018/0369261 A1   12/2018  Sato et al.

FOREIGN PATENT DOCUMENTS

JP      2007/238486      9/2007
WO   WO 2019/169496   9/2019

OTHER PUBLICATIONS

Google translation of JPH06219028A 1994; 9 pages. (Year: 1994).*
Napke, Excipients, Adverse Drug Reactions and Patient's Rights, Canadian Medical Association Journal, vol. 151(5):529-533, Sep. 1994.
McIlwraith, The Horse as a Model of Naturally Occurring Osteoarthritis, Bone & Joint Research, vol. 1(11):297-309, Nov. 2012.
U.S. Appl. No. 16/295,448, filed Mar. 7, 2019.
Search Report and Written Opinion in European Patent Application No. 19180410.3, dated Jul. 11, 2019.
Applicant's Response and Amendment in European Patent Application No. 19180410.3, filed Jan. 10, 2020.
Intent to Grant in European Patent Application No. 19180410.3, dated May 29, 2020.

* cited by examiner

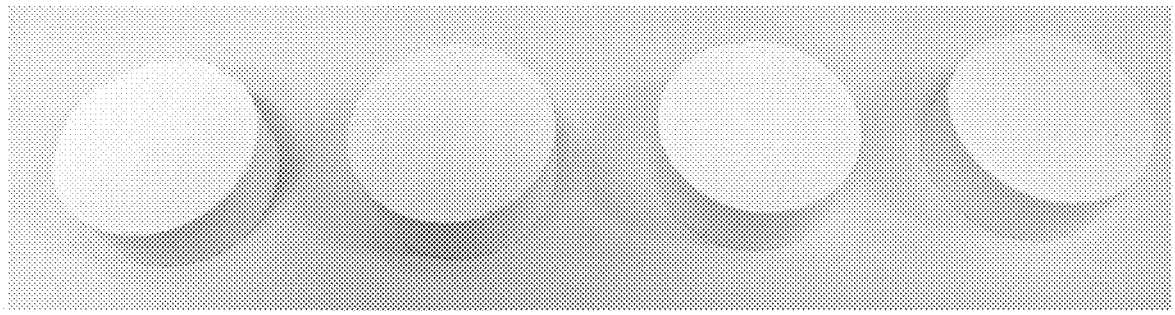

EXCIPIENT FREE N-ACETYL GLUCOSAMINE TABLETS AND METHOD OF MAKING

FIELD OF THE INVENTION

The present invention relates to glucosamine, and in particular to an excipient free N-Acetylglucosamine tablet and method of making excipient free N-Acetylglucosamine tablets.

BACKGROUND OF THE INVENTION

Drug, vitamin and supplement formulations include an active ingredient as well as additives, known as excipients or non-medicinal ingredients. An excipient is a pharmaceutical aid that may serve various purposes, such as, product identification e.g. colour; permit production on high speed equipment such as lubricants e.g. magnesium stearate; binders that hold a tablet together to permit handling and shipping; wicking agents that absorb moisture breaking up a compressed tablet in the stomach for predictable absorption; and coating agents that permit selective delivery to specific areas of the gastrointestinal tract. Excipients are present in solid oral medications.

Excipients are generally recognized as safe, innocuous, inert substances. There is growing evidence that excipients are not innocuous or inert and may cause adverse reactions (Ed Napke, "Excipients, adverse drug reactions and patients' rights", CMAJ 1994, page 529). When a patient exhibits an allergic reaction to a manufactured tablet it is automatically assumed that the allergy is to the active ingredient. This may not be the case. Pharmaceutical compendia such as the Canadian Compendium of Pharmaceuticals and Specialties have tables listing products that contain lactose, sulfites and tartrazines. These agents are known allergens because of the frequency of allergic occurrences. Excipients that have lower frequencies of allergic reactions do not make it on to the list. The problem of assuming that a person is allergic to the active and disregarding the excipients is two-fold: 1) the patient may exhibit allergies to many medications and be labelled as "a problem patient"; and 2) in case of serious illnesses the physician may be limited in the choice of medications available to treat a patient. This is of particular concern if there is a limited range of life saving alternatives, including antibiotics, and a patient with known allergies to drug formulations needs to take such antibiotics.

Since excipients make up as much as 30 to 50% of any tablet's volume, without excipients tablets of equivalent strength could be smaller. Where ever possible excipient free dosage forms would be ideal.

The dose or strength of an excipient free tablet can be determined simply by weighing the tablet since the only ingredient is the pharmaceutical active substance. A tablet free of excipients is amenable to a simplified testing protocol because it does not contain any interfering substances that could alter a chromatographic signature or infra-red spectra.

In order to exemplify the preparation of an excipient free pharmaceutical product N-Acetylglucosamine tablets for horses was selected. The administration of glucosamine to horses by the oral route is typically accomplished by powders added to the feed or by solutions given by gavage. The powders have multiple excipients, sometimes more than one active ingredient, and always include fillers, sweeteners, taste masking or flavoring agents. Powders present a challenge because it may not be possible to achieve dosing compliance for the following reasons:

1. The powder can be added to the horse's water but the horse may not drink all the water;
2. The powder can be added to the feed but the horse may not eat all its feed; and
3. Administration by gavage requires implements such as an irrigation syringe or a balling gun so that the medication is place on the back of the horses tongue, and the procedure is time consuming and uncomfortable for the horse.

Literature suggests that a majority of equine visits by veterinarians are for lameness and up to 60% of which will present with osteoarthiritis (CF Mcllwraith, "The horse as a model of naturally occurring osteoarthritis". Bone Joint Res 2012; 1:297-309). For Acute Management of Osteoarthritis, veterinarians may recommend anti-inflammatories, glycosaminoglycans, glucosamines, MSM, HA, corticosteroids, Interleukin-1 Receptor Antagonist Protein) or even PRP (Platelet-Rich Plasma injection).

Veterinarian clinics prescribe, offer, recommend or sell glucosamine related products.

Veterinarians usually only prescribe glucosamine products for horses when lame or determined to have osteoarthritis, but not for joint health generally since it's arduous to administer to horses—either by forcing a horse to consume glucosamine with excipients by gavage or through delivery in food or water which often means ingesting only part of a dose. Those who prescribe are not sure of the specific dose, or whether the horse will receive that dose with currently available products, all of which include excipients.

It would be advantageous to have an excipient free glucosamine formulation for treating lameness in horses which a horse would readily consume in a full dose.

SUMMARY OF THE INVENTION

In an embodiment of the present invention there is provided excipient free N-Acetylglucosamine tablets prepared by wetting N-Acetylglucosamine powder with 2% to 30% w/w water to form a mix, compressing the mix into wells of a mold to form individual wet tablets in each of the wells, expressing the wet tablets, and allowing the water to evaporate from the wet tablets. The excipient free N-Acetylglucosamine tablets may be prepared with 4% to 15% w/w sterile water. The water may evaporate from the wet tablets by placing the wet tablets in a drying chamber. The amount of N-Acetylglucosamine is between 200 mg to 20 grams. The amount of N-Acetylglucosamine may be 10 grams in an embodiment of the invention particularly suitable for horses.

An embodiment of the present invention relates to a method of making excipient free N-Acetylglucosamine tablets by wetting N-Acetylglucosamine powder with 2% to 30% w/w water to form a mix, compressing the mix into wells of a mold to form individual wet tablets in each of the wells, expressing the wet tablets, and allowing the water to evaporate from the wet tablets. The method may use 4% to 15% w/w sterile water to form the mist in an embodiment of the invention, and further the method may include use of a drying chamber to aid evaporation. The amount of N-Acetylglucosamine is between 200 mg to 20 grams, and 10 grams is particularly suitable for horses.

BRIEF DESCRIPTION OF THE FIGURES

These and other aspects of the present invention will be apparent from the brief description of the drawings and the following detailed description in which:

FIG. 1 is excipient free 10 gram tablets of N-Acetylglucosamine of an embodiment of the present invention.

DETAILED DESCRIPTION OF THE INVENTION

An embodiment of the present invention is an excipient free glucosamine and an embodiment of the method of the present invention is a process for preparing an excipient free tablet by mixing glucosamine with water, compressing the resultant mass into a mold, expressing it into individual units, and placing the tablets in a drying chamber or simply in a room so that the water is permitted to evaporate. This process allows the production of glucosamine tablets free from excipients.

In formulating the glucosamine tablets of the present invention, salt free N-Acetylglucosamine was chosen to develop a chewable tablet. N-Acetylglucosamine is slightly sweet and horses and most mammals enjoy a sweet taste. Using the active ingredient of N-Acetylglucosamine, it was necessary to determine the correct solvent, as well as the correct amount of the correct solvent, and the correct rate of drying and elimination of the solvent. Water was found to be an effective solvent in an embodiment of the present invention.

To prepare the excipient free tablets of N-Acetylglucosamine of the present invention, N-Acetylglucosamine powder is mixed with an amount of water of 2% to 30% w/w, the resultant mixture is placed in the wells of a tablet triturate mold of the desired tablet size and compressed with a punch and die, and the resultant tablets are dried until the solvent evaporates off.

In an embodiment of the present invention, excipient free 10 g tablets of N-Acetylglucosamine are prepared by mixing N-Acetylglucosamine powder with 5% w/w sterile water, compressing the mixture into a tablet triturate mold with wells for producing 10 g tablets, and drying the resultant tablets.

In an embodiment of the present invention, there is a method of making a glucosamine tablet without excipients, using a specific form of glucosamine, N-Acetylglucosamine, since it has a sweet flavour. The resulting glucosamine tablet has the following characteristics:
1. Contains N-Acetylglucosamine as the sole ingredient;
2. A discrete dose (1 tablet) is deliverable which does not require skill, thinking or effort on the part of the caregiver;
3. Pleasant tasting to ensure consumption of the whole product;
4. Is not dependent on another 'vehicle' to encourage consumption (e.g. water/meal/gavage);
5. Does not require a coating for the tablet to maintain integrity; and
6. Guarantees animal compliance/adherence because it is easy to ensure that the whole dose is taken, and it would be obvious if the dose is not taken since the tablet or remains of the tablet would be fully observable.

The excipient free tablet of the present invention is consumable by horses, other animals and humans and the size of the tablet may be determined by the size of the consumer and the dose required by the consumer and condition being treated, for example, 200 mg to 20 grams.

In an embodiment of the present invention excipient free glucosamine tablets are made with a mixture of N-Acetylglucosamine and 2.5% to 15% w/w sterile water compressed in a tablet triturate mold.

In a further embodiment of the present invention, 10 gram glucosamine tablets are made with a mixture of N-Acetylglucosamine and 4% to 15% w/w sterile water compressed in a tablet triturate mold.

In a further embodiment of the present invention, 10 gram glucosamine tablets are made with a mixture of N-Acetylglucosamine and 5% sterile water compressed in a tablet triturate mold to a 1.5 cm thick tablet that is 3.5 cm in diameter.

The following examples show the development of the excipient free tablets of N-Acetylglucosamine and methods of making same. The 10 gram tablet was developed for horses since they are large and need a bigger dose. A 0.5 to 2 gram tablet size or lozenge is more suitable for human use, or companion animal use and still has the benefit of being excipient free and edible. The excipient free tablet can be adjusted to the requirements of an animal based on the size and dose requirement of a given animal.

EXPERIMENTS

The starting point of the method for preparing an excipient free tablet is to mix an active pharmaceutical ingredient with a solvent, form the resultant mass into a tablet shape and heat it so that the solvent evaporates leaving a solid tablet behind. The choice of the solvent is dependent on the pharmaceutical ingredient, since the dried mass, or tablet, of the pharmaceutical agent needs to retain its form even when packaged in a suitable container and after being removed from the container for administration. The solvent should dissolve some of the active pharmaceutical ingredient so that during shaping and subsequent evaporation the tablet so formed will have the required mechanical strength to be packaged into and removed from a container.

Trials 1-3—N-Acetylglucosamine Excipient Free Tablet Trials

Initial trials involved testing whether N-Acetylglucosamine without excipients could be formed into a tablet shape that retained its shape when the tablet was 1) removed from the mold; 2) during evaporation of the solvent; 3) during packaging into a container; 4) during shipping; and 5) during handling by the end user. N-Acetylglucosamine was mixed with 30% purified water to form a wet mass that was formed using a scoop and dried in an oven at 170° F. for 1 hour. This formed well defined N-Acetylglucosamine ½ spheres but they were quite friable with handling.

Similar, independent trials were performed using a silicon ice-cube tray. A wet mass was formed using ~30% w/w purified water. This forms a crumbly mixture that can be compacted by hand. When dried, they formed friable cubes that were within ±10% of target weight of 10 g, but again crumbled with handling.

Trial 4-N-Acetylglucosamine Pellets using a pellet press

Recognizing that N-Acetylglucosamine could be formed into solid dosage forms, further tests were performed to explore how to make the final solid dosage form less friable. The hope was that under compression the mass would form a more cohesive and solid dosage form.

Using a pellet press (from Par Instruments), tests were done compressing wetted N-Acetylglucosamine with the addition of either 50% purified water or 10% purified water and as pure dry powder. Purified water concentrations were selected to bracket previous trial concentrations (30%) to explore how purified water changes how the N-Acetylglucosamine behaves once dried.

With 50% w/w purified water added, N-Acetylglucosamine compressed nicely with a lot of purified water squeezing out of the mix. A pellet was formed that, once dry, formed a hard, robust, less-friable dosage form with consistency similar to chalk.

With 10% w/w purified water, less purified water squeezed out yet the N-Acetylglucosamine still compressed well. Produced a good pellet similar to the 50% but observationally less friable than the same.

Pure N-Acetylglucosamine without the addition of purified water did not compress at all.

Trial 5—Crude Density Calculations

Calculations were made regarding whether N-Acetylglucosamine tablets could be produced on a commercial tablet machine. Crude calculations were performed to get a sense of tablet dimensions that would be required for the target weight of 10 grams. Volume and density calculations were extrapolated from the results in Trial 4 and from tablet volume and weight of commercial glucose tablets, containing excipients (the largest tablets available commercially).

Trial 6—200 mg Tablet

Commercial manual tablet triturate molds are only available up to 200 mg tablet size (0.181 ml), which is what was used for this experiment. Further, different solvents were used to see what could work and whether ethanol could be used.

In this trial, a wet mass of N-acetylglucosamine was made with 15% w/w purified water and molded using the tablet triturate mold. These tablets were allowed to dry. The final tablet was solid, held shape, hard, not very friable, and acceptable to the palate, remaining sweet.

A wet mass of N-acetylglucosamine was also formed using ethanol, once dried the tablets were very friable and broke apart easily when handled. The resultant tablets were quite bitter tasting in contrast to the tablets made with water.

For both samples, tablets were produced well within ±5% of target weight.

Recognizing that N-Acetylglucosamine could be produced by molding a wetted mass with purified water and dried, calculations were performed to extrapolate and estimate a mold that could potentially produce a 10 g tablet. These calculations were based on density calculations from previous trials and on assumptions of upper limits of commercial automatic tablet press die dimensions.

A custom made aluminum tablet mold was made by estimating well dimensions in order to achieve a 10 g tablet; the desired target dose.

Trial 7—Large Tablet Mold

N-Acetylglucosamine tablets were produced using the custom-made tablet mold. N-Acetylglucosamine was wetted with 10% w/w purified water. The mold was filled with the wetted mixture calculated at a theoretical fill weight of 10 g (on a dry basis). The tablets were expelled and allowed to air dry. Tablets weights were assessed and within ±10% of the mean of the tablet weight. Mean tablet weight was 5.11 grams which is below target weight.

Trial 8—Applying Compression Forces to the Custom Mold

The goal with this trial was much the same as in trial 6, but compression forces were applied to attempt to fill the cavities in the custom mold with more material and achieve something closer to 10 g. A mix was made with 10% w/w purified water and the wells filled with the mix. Using a hammer and punch that fits the die, N-acetylglucosamine mix was compacted into the well with repeated fillings. Once removed and dried the tablets were weighed. Mean weight was 5.62 grams ±5.7%, again below the target weight.

Tablets were quite hard, non-friable, but easy to bite into. After a few days it was noticed that the surface of the tablets was discoloured, turning a yellow brown colour.

Trial 9—Taste Test on Horses

Establishing that a tablet could be produced, it was necessary to learn whether they would be palatable to horses. Tablets were produced as in Trial 8 (10% w/w purified water) and tested on horses, with the permission of horse owners and trainer, and the horses ate the tablets readily directly from hand. Horse owners and trainers felt that the glucosamine tablet format was unique and represented a beneficial method of administering glucosamine to a horse.

Trial 10—Preparing 10 Gram N-Acetylglucosamine Tablets

A machine was built with punches and dies large enough to accommodate greater volumes of N-Acetylglucosamine. N-acetylglucosamine, tablets were formed using the new machine. Sterile water at 15%, 10%, 5% concentrations was used to prepare excipient free tablets.

The resulting tablets compressed to a 1.5 cm thickness and were well formed as seen in FIG. 1. Mean weight for the tablets were 10.4, 10.5, and 10.01 grams for the 15%, 10%, and 5% w/w water mixes, respectively, after evaporation of the water solvent. After solvent evaporation the tablets made with the 15% w/w water mixes were much more friable than those using only 5% water. The tablets made with the 5% w/w water mix were well defined, with clean edges and much whiter than tablets produced with higher percentage of water. It is understood that a 10 gram tablet of N-Acetylglucosamine of an embodiment of this invention includes a tablet of 9.5 grams to 10.5 grams.

Trial 11—N-Acetylglucosamine Tablets Made Using a 2.5% w/w Water Mix

In an effort to minimize water content, experiments were conducted to explore the minimum water content required as a % of N-Acetylglucosamine w/w. In this trial, water was added at 2.5% w/w to N-Acetylglucosamine and tablets formed as in other trials using the new custom machine. The resultant tablets were quite friable and dusty when handled. They broke apart easily when handled and are not suitable for packaging or shipping or handling. The final tablets did not meet the hardness and friability characteristics desired.

Trial 12—N-Acetylglucosamine at 4% w/w Water Mixes

Trial 11 produced N-Acetylglucosamine tablets using 2.5% w/w water which did not meet the characteristics sought. At that point the 5% w/w was the best tablet produced from physical characteristics, palatability and weight consistency standpoints. To explore water content between that of 2.5% and 5% this trial looked at producing tablets at 4% w/w water. The resultant tablets formed well with acceptable demarcated edges and break with ease in hand with acceptable hardness and friability but had a lot of free powder on the outside.

While embodiments of the invention have been described in the detailed description, the scope of the claims should not be limited by the preferred embodiments set forth in the examples, but should be given the broadest interpretation consistent with the description as a whole.

All publications cited in this specification are incorporated herein by reference, as well as Canadian Patent Application No. 3,008,722. While the invention has been described with reference to particular embodiments, it will be appreciated that modifications can be made without departing from the spirit of the invention. Such modifications are intended to fall within the scope of the appended claims.

What is claimed is:

1. A method of making excipient free N-Acetylglucosamine chewable tablets by wetting N-Acetylglucosamine powder with 4% to 15% w/w purified water to form a mix, compressing the mix into wells of a mold to form individual wet tablets in each of the wells, expressing the wet tablets, and allowing the water to evaporate from the wet tablets.

2. The method of claim 1, in which allowing the water to evaporate from the wet tablets consists of placing the wet tablets in a drying chamber.

3. The method of claim 1, in which the amount of N-Acetylglucosamine in the excipient free N-Acetylglucosamine tablets is between 200 mg to 20 grams.

4. The method of claim 1, in which the amount of N-Acetylglucosamine in the excipient free N-Acetylglucosamine tablets is 10 grams.

* * * * *